(12) United States Patent
Lee et al.

(10) Patent No.: US 10,413,275 B2
(45) Date of Patent: Sep. 17, 2019

(54) ULTRASOUND PROBE AND MANUFACTURING METHOD THEREOF

(71) Applicant: SAMSUNG ELECTRONICS CO., LTD., Suwon-si (KR)

(72) Inventors: Eunsung Lee, Hwaseong-si (KR); Youngil Kim, Suwon-si (KR); Jong Keun Song, Yongin-si (KR); Minseog Choi, Seoul (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 191 days.

(21) Appl. No.: 14/732,894

(22) Filed: Jun. 8, 2015

(65) Prior Publication Data
US 2015/0374336 A1    Dec. 31, 2015

(30) Foreign Application Priority Data

Jun. 25, 2014    (KR) .................. 10-2014-0077814

(51) Int. Cl.
| | | |
|---|---|---|
| *A61B 8/00* | (2006.01) | |
| *A61B 8/14* | (2006.01) | |
| *G01S 7/52* | (2006.01) | |
| *B06B 1/02* | (2006.01) | |
| *G01S 15/89* | (2006.01) | |
| *A61B 8/08* | (2006.01) | |

(52) U.S. Cl.
CPC .............. *A61B 8/4494* (2013.01); *B06B 1/02* (2013.01); *G01S 7/5208* (2013.01); *G01S 15/8915* (2013.01); *A61B 8/0891* (2013.01); *A61B 8/14* (2013.01); *A61B 8/4444* (2013.01); *B06B 2201/76* (2013.01)

(58) Field of Classification Search
CPC ................... A61B 8/444483; A61B 8/4494
See application file for complete search history.

(56) References Cited

U.S. PATENT DOCUMENTS

| | | | |
|---|---|---|---|
| 2010/0255623 A1* | 10/2010 | Huang ................. | B06B 1/0292 438/51 |
| 2013/0106868 A1* | 5/2013 | Shenoy ............... | B81C 1/00269 345/501 |
| 2013/0214641 A1 | 8/2013 | Eggen et al. | |

OTHER PUBLICATIONS

"Integration of 2D CMUT Arrays with Front-End Electronics for Volumetric Ultrasound Imaging" by I.O. Wygant et al. IEEE Trans Ultra Ferr Freq Cont. vol. 55, No. 2, pp. 327-342. Feb. 2008.*

* cited by examiner

*Primary Examiner* — Tse W Chen
*Assistant Examiner* — Jason M Ip
(74) *Attorney, Agent, or Firm* — Sughrue Mion, PLLC

(57) ABSTRACT

Disclosed herein is an ultrasound probe including a transducer array configured to generate ultrasonic waves, an integrated circuit disposed on a back surface of the transducer array by using an adhesive member, a printed circuit board connected to the integrated circuit and configured to output a signal to the integrated circuit, and a pad bridge disposed on front surfaces of the printed circuit board and the integrated circuit by using the adhesive member and configured to electrically connect the printed circuit board with the integrated circuit. An area of a region of the ultrasound probe contacting the human body may be reduced without reducing the size of the transducer array, and the integrated circuit and the printed circuit board may be integrally connected by using the adhesive member.

12 Claims, 12 Drawing Sheets

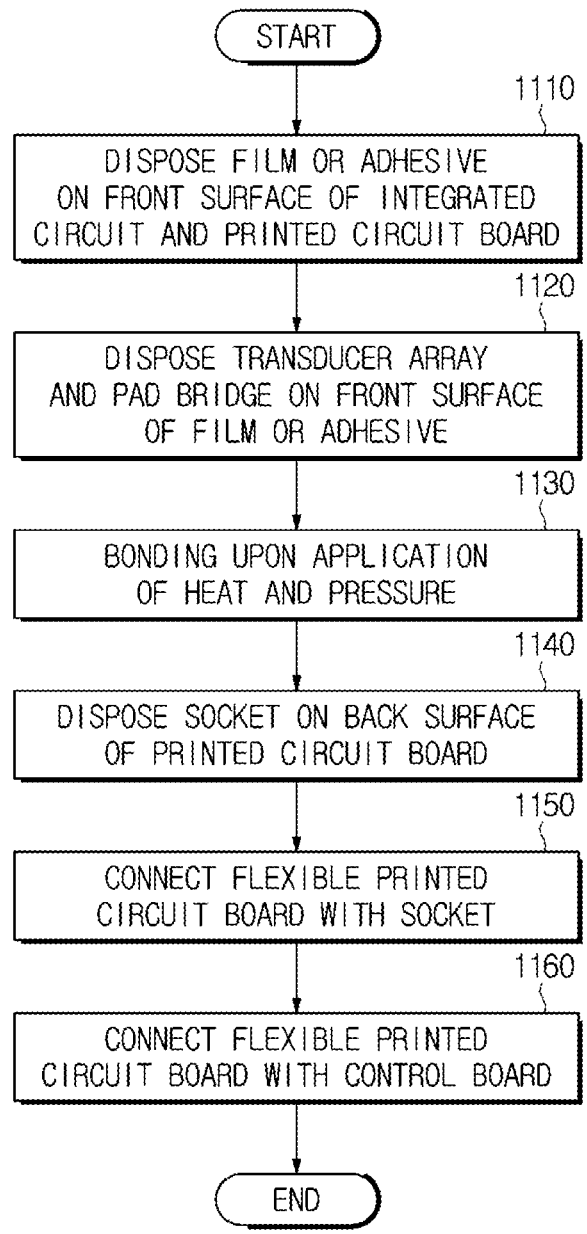

ULTRASOUND PROBE AND MANUFACTURING METHOD THEREOF

CROSS-REFERENCE TO RELATED APPLICATION(S)

This application claims priority from Korean Patent Application No. 10-2014-0077814, filed on Jun. 25, 2014 in the Korean Intellectual Property Office, the disclosure of which is incorporated herein by reference in its entirety.

BACKGROUND

1. Field

Exemplary embodiments relate to ultrasound probes.

2. Description of the Related Art

An ultrasonic imaging apparatus is an apparatus which is configured to acquire a soft tissue tomogram or a blood stream image in a non-invasive method by emitting ultrasonic waves toward a target region in an object from the surface of the object and receiving echo ultrasonic waves reflected by the target region.

Since the ultrasonic imaging apparatus is small and inexpensive, displays an image in real time, and provides high safety owing to no X-ray exposure, as compared to other image diagnostic apparatuses such as an X-ray diagnosis apparatus, a computerized tomography (CT) scanner, a magnetic resonance imaging (MRI) apparatus, and a nuclear medicine diagnostic apparatus. Thus, the ultrasonic imaging apparatus has been widely used for performing heart diagnosis, celiac diagnosis, urinary diagnosis, and obstetric diagnosis.

The ultrasonic imaging apparatus includes an ultrasound probe which is configured to emit ultrasonic waves toward an object and to receive echo ultrasonic waves reflected by the object in order to acquire an image of the inside of the object.

SUMMARY

Therefore, it is an aspect of one or more exemplary embodiments to provide an ultrasound probe in which a transducer array and a pad bridge are connected to an integrated circuit and a printed circuit board.

It is another aspect of one or more exemplary embodiments to provide an ultrasound probe in which a transducer array and a flexible printed circuit board are connected to an integrated circuit and a printed circuit board.

Additional aspects will be set forth in part in the description which follows and, in part, will be obvious from the description, or may be learned by practice of the exemplary embodiments.

In accordance with one aspect of one or more exemplary embodiments, an ultrasound probe includes a transducer array configured to generate ultrasonic waves, an integrated circuit disposed on a back surface of the transducer array by using an adhesive member, a printed circuit board connected to the integrated circuit and configured to output a signal to the integrated circuit, and a pad bridge disposed on front surfaces of the printed circuit board and the integrated circuit by using the adhesive member and configured to electrically connect the printed circuit board with the integrated circuit.

The adhesive member may include at least one from among an anisotropic conductive film, an isotropic conductive film, and a non-conductive film.

The adhesive member may include at least one from among an anisotropic conductive adhesive, an isotropic conductive adhesive, and a non-conductive adhesive.

The transducer array, the pad bridge, the integrated circuit, and the printed circuit board may be bonded together by the adhesive member by using an application of heat and pressure.

The printed circuit board may include a cavity configured to support the integrated circuit.

The integrated circuit may include a first plurality of electrodes and the printed circuit board may include a second plurality of electrodes, and the pad bridge may be further configured to electrically connect the first plurality of electrodes with the second plurality of electrodes by using the adhesive member.

The ultrasound probe may further include a flexible printed circuit board which includes a first end connected to the back surface of the printed circuit board and which is configured to output a signal to the printed circuit board, and a control board connected to a second end of the flexible printed circuit board and configured to output a signal to the printed circuit board via the flexible printed circuit board.

In accordance with another aspect of one or more exemplary embodiments, an ultrasound probe includes a transducer array configured to generate ultrasonic waves, an integrated circuit disposed on a back surface of the transducer array by using an adhesive member, a printed circuit board connected to the integrated circuit and configured to output a signal to the integrated circuit, and a flexible printed circuit board which includes a first end connected to front surfaces of the printed circuit board and the integrated circuit by using the adhesive member.

The adhesive member may further include at least one from among an anisotropic conductive film, an isotropic conductive film, and a non-conductive film.

The adhesive member may further include at least one from among an anisotropic conductive adhesive, an isotropic conductive adhesive, and a non-conductive adhesive.

The transducer array, the flexible printed circuit board, the integrated circuit, and the printed circuit board may be bonded together by the adhesive member by using an application of heat and pressure.

The printed circuit board may include a cavity configured to support the integrated circuit.

The flexible printed circuit board may include an empty region, and the empty region is a region in which the transducer array is bonded to the integrated circuit.

In accordance with another aspect of one or more exemplary embodiments, a method for manufacturing an ultrasound probe includes disposing an adhesive member on front surfaces of an integrated circuit and a printed circuit board, disposing a transducer array configured to generate ultrasonic waves and a pad bridge configured to connect the integrated circuit with the printed circuit board on a front surface of the adhesive member, and bonding the integrated circuit, the printed circuit board, the pad bridge, and the transducer array by applying at least one from among heat and pressure.

The method may further include disposing a socket on a back surface of the printed circuit board, and disposing a flexible printed circuit board which includes a first end connected to the socket, wherein the flexible printed circuit board is configured to output a signal to the printed circuit board.

The bonding may include bonding in a vacuum environment.

BRIEF DESCRIPTION OF THE DRAWINGS

These and/or other aspects will become apparent and more readily appreciated from the following description of exemplary embodiments, taken in conjunction with the accompanying drawings of which:

FIG. 12 is a flowchart illustrating a method of manufacturing an ultrasound probe, according to an exemplary embodiment.

DETAILED DESCRIPTION

Figure 1:
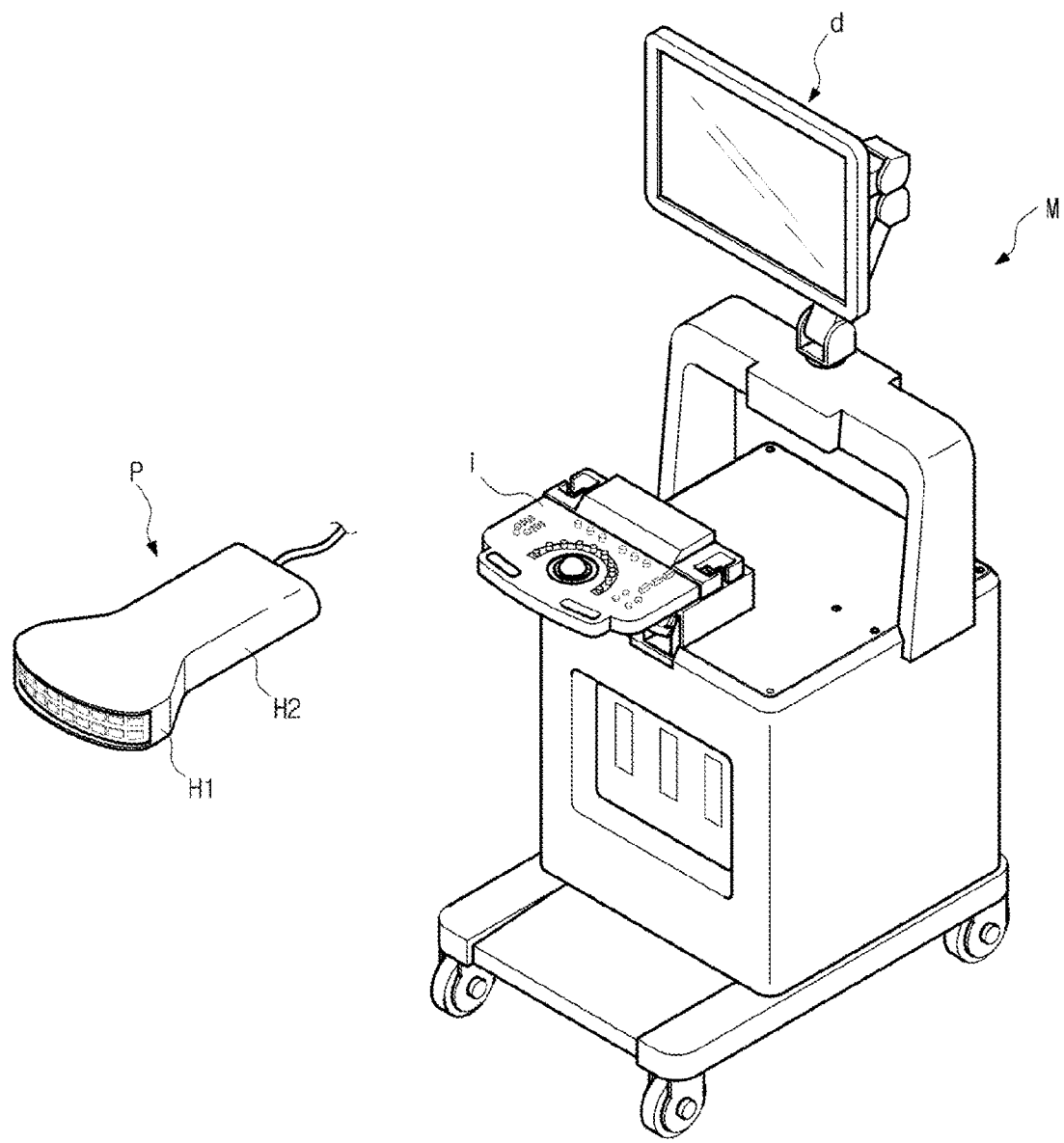
FIG. 1 is a perspective view exemplarily illustrating a configuration of an ultrasonic imaging apparatus.

Reference will now be made in detail to exemplary embodiments, examples of which are illustrated in the accompanying drawings, wherein like reference numerals refer to like elements throughout. In the description of the exemplary embodiments, certain detailed explanations of related art are omitted when it is deemed that they may unnecessarily obscure the essence of the exemplary embodiments. It will be understood that although the terms "first", "second", etc. may be used herein to describe various components, these components should not be limited by these terms. These components are only used to distinguish one component from another.

Hereinafter, exemplary embodiments will be described in detail with reference to the accompanying drawings.

Figure 2:
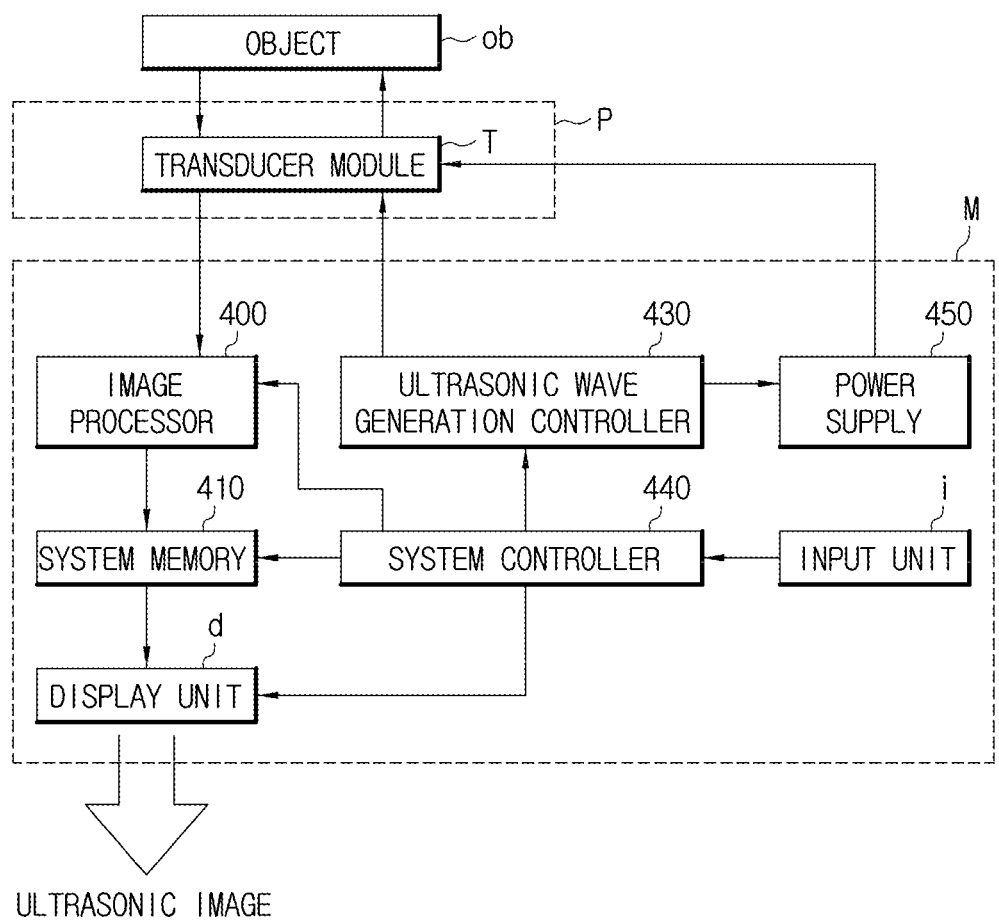
FIG. 2 is a block diagram exemplarily illustrating the ultrasonic imaging apparatus.

FIG. 1 is a perspective view exemplarily illustrating a configuration of an ultrasonic imaging apparatus. FIG. 2 is a block diagram exemplarily illustrating the ultrasonic imaging apparatus.

Referring to FIGS. 1 and 2, an ultrasonic imaging apparatus includes an ultrasound probe P configured to emit ultrasonic waves toward an object ob, receive echo ultrasonic waves from the object ob, and convert the received echo ultrasonic waves into electric signals (hereinafter, referred to as ultrasonic signals), and a main body M configured to generate an ultrasonic image based on the ultrasonic signals. As illustrated in FIG. 1, the main body M may be a workstation connected to the ultrasound probe P and including an input unit (also referred to herein as an "input device") i and a display unit (also referred to herein as a "display device" and/or as a "display") d.

As illustrated in FIG. 2, the main body M includes an image processor 400 which is configured to generate an image based on an ultrasonic signal output from the ultrasound probe P, a system memory 410 which is configured to store the ultrasonic image generated by the image processor 400, a display unit d which is configured to display the ultrasonic image generated by the image processor 400 or the ultrasonic image stored in the system memory 410, an ultrasonic wave generation controller 430 which is configured to control an emission of ultrasonic waves of a transducer module T, a power supply 450 which is configured to apply a predetermined alternating current to the transducer module T, an input unit i through which an instruction or command to control the ultrasonic imaging apparatus is input by a user, and a system controller 440 which is configured to control an overall operation of the ultrasonic imaging apparatus by controlling the ultrasonic wave generation controller 430, the image processor 400, the system memory 410, and the display unit d.

The image processor 400 generates an image such that a user, e.g., a doctor or a patient, visually checks the object ob, e.g., the inside of a human body, based on the ultrasonic signal.

The image processor 400 transmits the ultrasonic image generated using the ultrasonic signal to the system memory 410 and/or to the display unit d.

In addition, the image processor 400 may further perform an additional image processing of the ultrasonic image. For example, the image processor 400 may further perform a post-processing operation, such as, for example, a correction or re-adjustment of contrast, brightness, and/or sharpness of the ultrasonic image.

In addition, one region of the ultrasonic image may be distinguished from the other region by using known techniques such as using different colors or a marker, or a 3-dimensional (3D) ultrasonic image may be created by generating a plurality of ultrasonic images. This additional image processing of the image processor 400 may be performed in accordance with predetermined settings or an instruction of command of the user input through the input unit i.

The system memory 410 stores the ultrasonic image generated by the image processor 400 or the post-processed ultrasonic image, and the display unit d displays the ultrasonic image generated by the image processor 400 or the ultrasonic image stored in the system memory 410 such that the user may visually check an inner structure or tissues of the object ob.

The ultrasonic wave generation controller 430 generates a transmit pulse in accordance with the command of the system controller 440, and transmits the transmit pulse to the transducer module T. The transducer module T generates ultrasonic waves in accordance with the transmit pulse which is output from the ultrasonic wave generation controller 430 and emits the ultrasonic waves toward the object ob.

In addition, the ultrasonic wave generation controller 430 may generate a separate control signal for the power supply 450 such that the power supply 450 may apply a predetermined alternating current to the transducer module T.

The system controller 440 controls the overall operation of the ultrasonic imaging apparatus such as the ultrasonic wave generation controller 430, the image processor 400, the system memory 410, and the display unit d.

According to the illustrated exemplary embodiment, the system controller 440 may control the operation of the ultrasonic imaging apparatus in accordance with the predetermined settings or after generating a predetermined control command according to an instruction or command of the user input through the input unit i.

The input unit i receives an instruction or command from the user to control the ultrasonic imaging apparatus. The input unit i may include a user interface, such as, for example, any one or more of a keyboard, mouse, trackball, touch screen, and/or paddle.

The ultrasound probe P collects information regarding a target region of the object ob by using ultrasonic waves.

Referring to FIG. 2, the ultrasound probe P includes the transducer module T that generates ultrasonic waves, emits the ultrasonic waves toward the target region of the object ob, and receives echo ultrasonic waves.

The transducer module T generates ultrasonic waves in accordance with a pulse signal or alternating signal applied thereto and emits the ultrasonic waves toward the object ob. The ultrasonic waves emitted to the object ob are reflected by the target region. The transducer module T receives reflected echo ultrasonic waves and converts the received echo ultrasonic waves into electric signals, thereby generating ultrasonic signals.

The transducer module T receives power from an external power supplying device or an internal charge storage device, such as a battery. When power is supplied, a piezoelectric vibrator or a thin film constituting the transducer module T vibrates. The transducer module T emits the ultrasonic waves generated by vibration of the piezoelectric vibrator or the thin film to the object ob. When the echo ultrasonic waves reflected by the object ob are received, the piezoelectric vibrator or the thin film constituting the transducer module T vibrates in accordance with the echo ultrasonic waves. The transducer module T generates alternating current having a frequency corresponding to a vibration frequency of the piezoelectric vibrator or the thin film, thereby converting ultrasonic waves into electric signals (hereinafter, referred to as ultrasonic signals).

Figure 3:
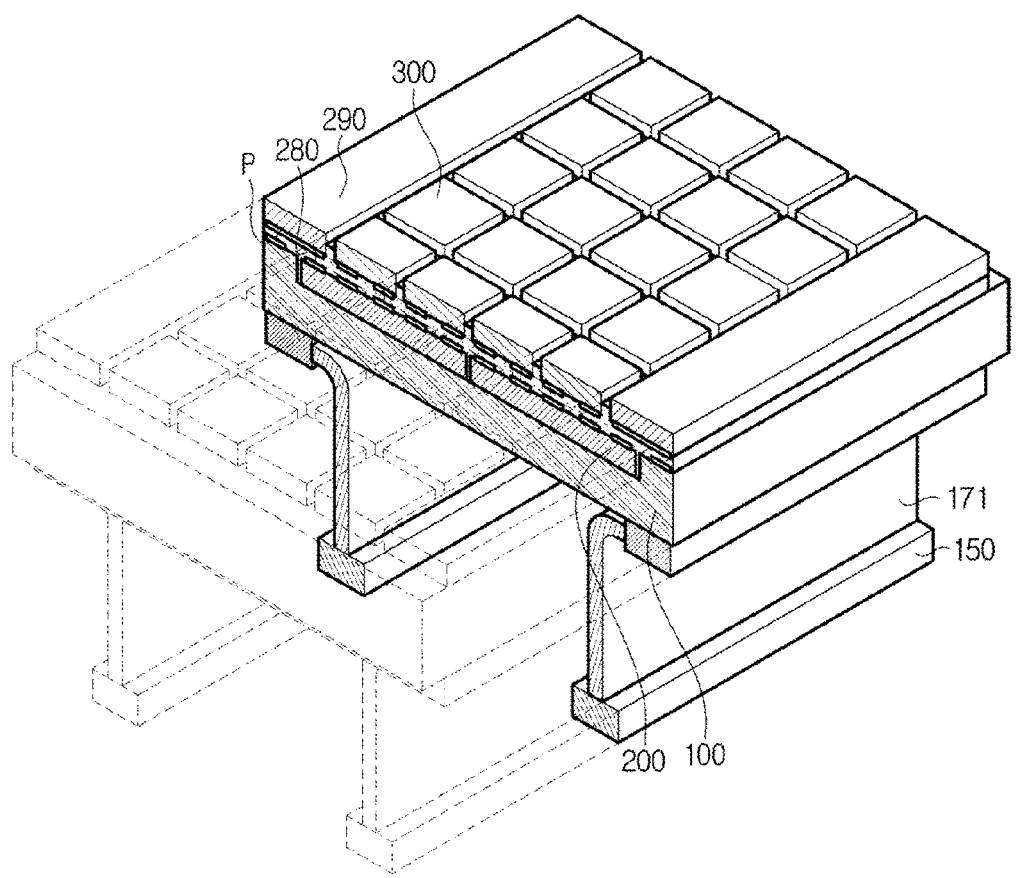
FIGS. 3 and 4 are perspective views illustrating examples of a transducer module of an ultrasound probe, according to an exemplary embodiment.
Figure 4:
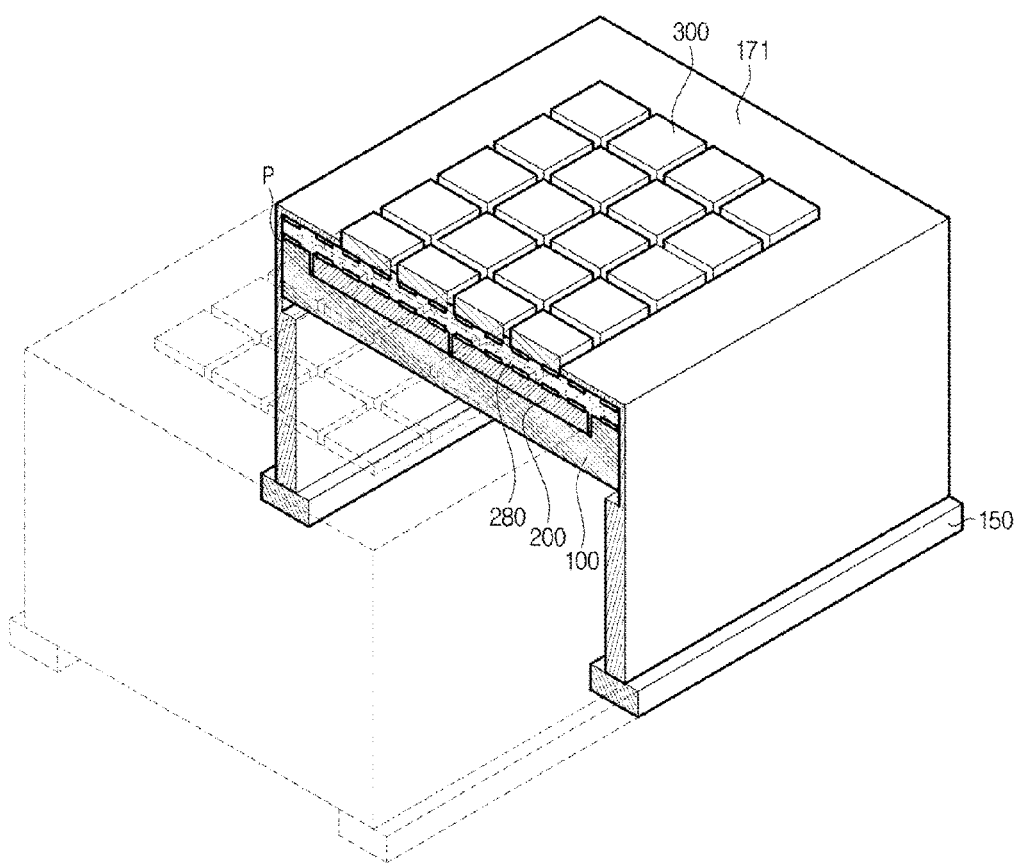
Figure 5:
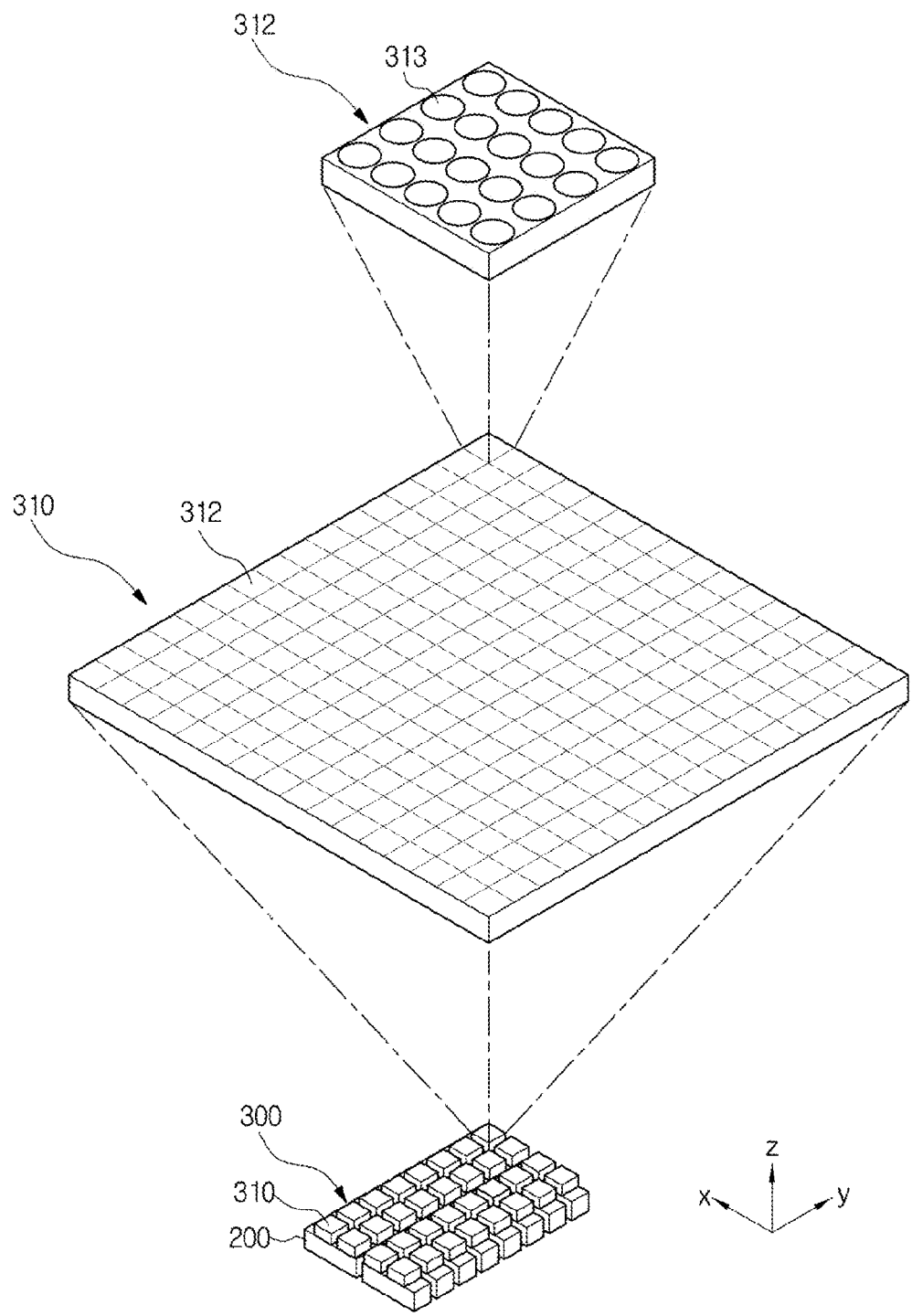
FIG. 5 is an enlarged diagram illustrating a concept of configurations of transducer arrays of the transducer modules of FIGS. 3 and 4.
Figure 6:
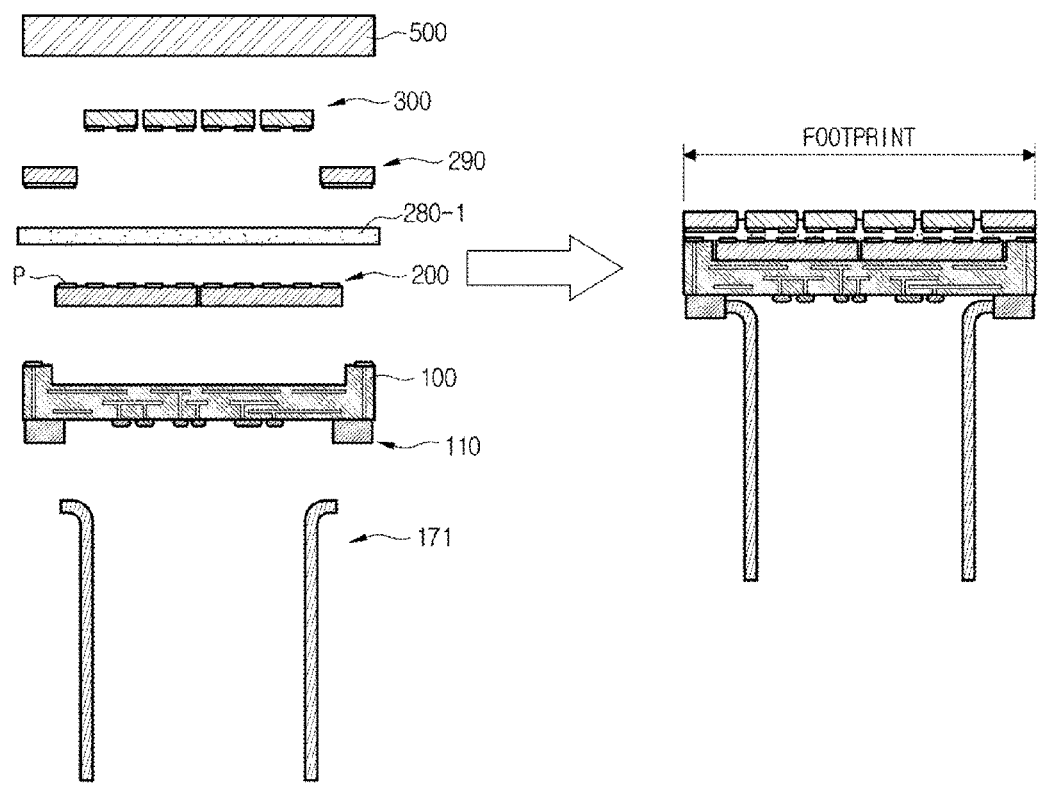
FIGS. 6, 7, and 8 are cross-sectional views of examples of the transducer modules of the ultrasound probe, according to the illustrated exemplary embodiment.
Figure 7:
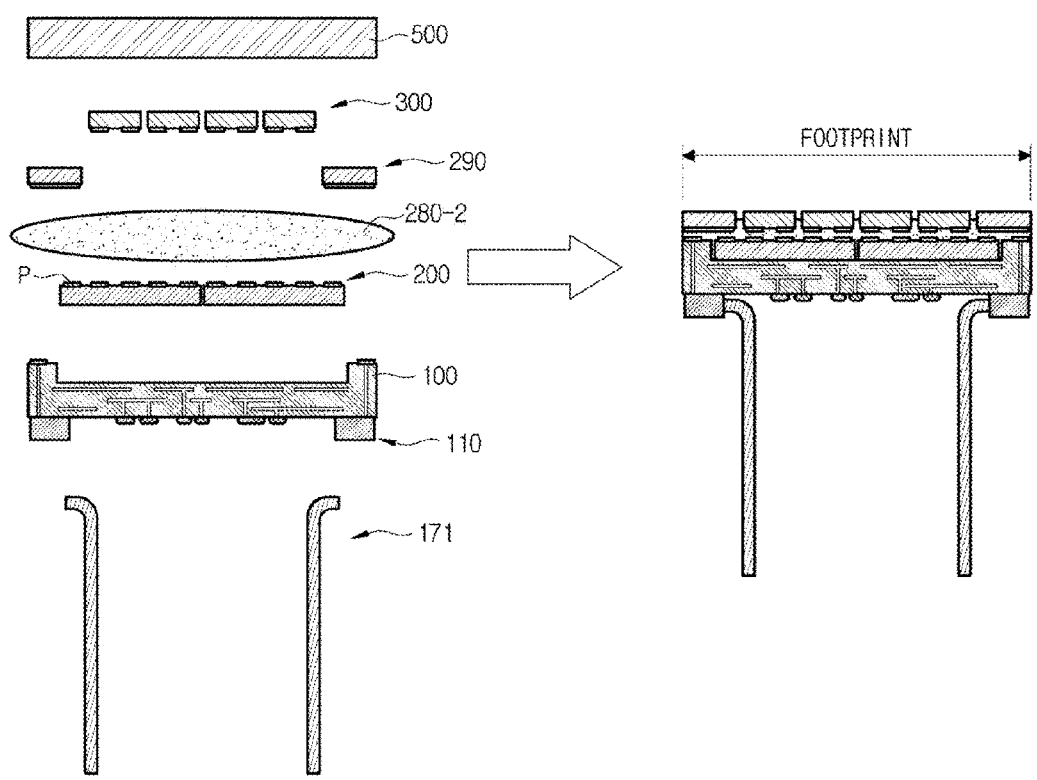
Figure 8:
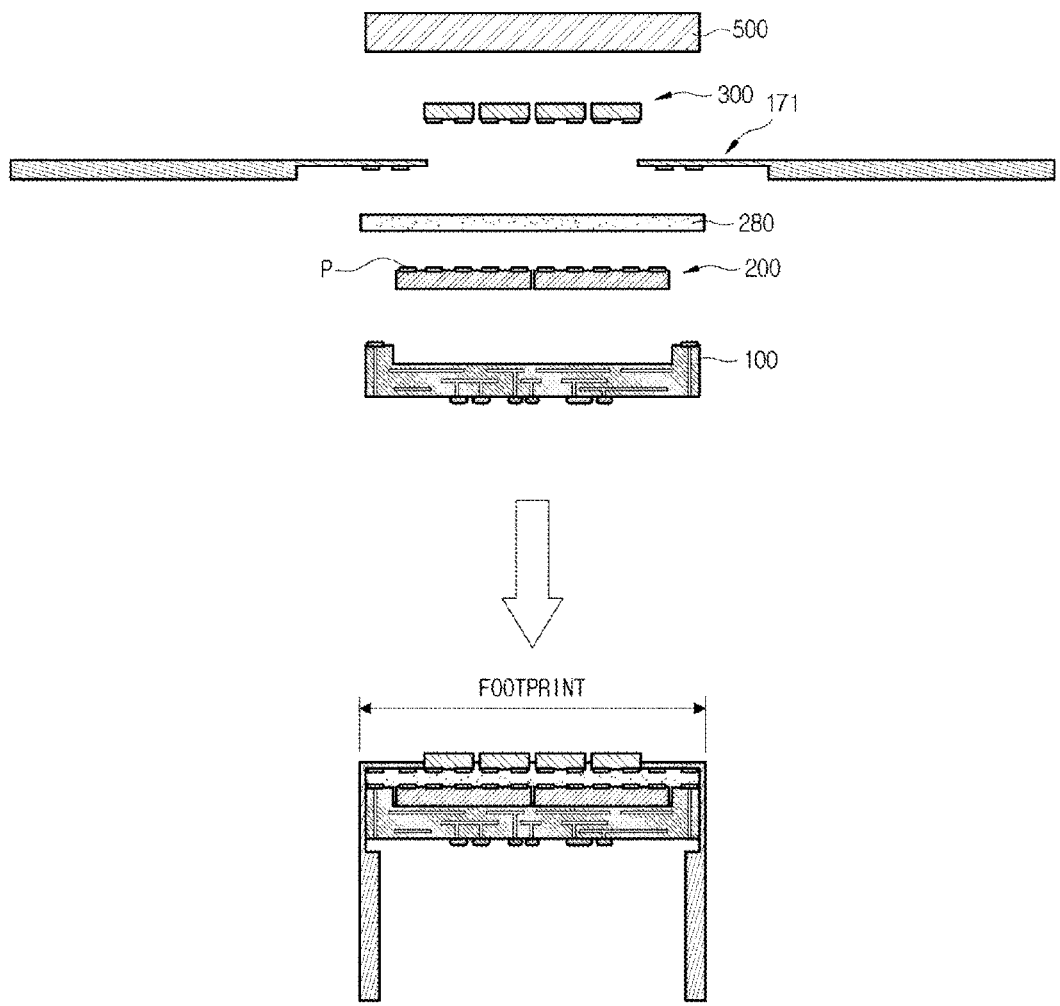

Hereinafter, the transducer module T will be described in more detail with reference to FIGS. 3 to 8. FIGS. 3 and 4 are perspective views illustrating examples of the transducer module of the ultrasound probe, according to the illustrated exemplary embodiment. FIG. 5 is an enlarged diagram illustrating a concept of configurations of transducer arrays of the transducer modules of FIGS. 3 and 4. FIGS. 6, 7, and 8 are cross-sectional views of examples of the transducer module of the ultrasound probe, according to the illustrated exemplary embodiment.

In particular, FIG. 6 is a cross-sectional view of a transducer module of an ultrasound probe bonded using a film 280-1, FIG. 7 is a cross-sectional view of a transducer module of an ultrasound probe bonded using an adhesive 280-2, and FIG. 8 is a cross-sectional view of a transducer module of an ultrasound probe realized using a flexible printed circuit board 171 instead of a pad bridge 290.

Referring to FIG. 3, the transducer module T includes: a transducer array 300 configured for transmitting and receiving ultrasonic waves; a pad bridge 290 which includes wiring blocks configured for electrical connection between integrated circuits 200 and a printed circuit board 100; the integrated circuits 200 to which the transducer array 300 is bonded; the printed circuit board 100 and a flexible printed circuit board 171 which connect the integrated circuits 200 with a control board 150 in order to output a transmit signal output from the control board 150 to the integrated circuits 200, and the control board 150 configured for outputting the transmit signal for generating ultrasonic waves to the integrated circuits 200.

The transducer array 300 includes a plurality of transducer elements 312 that transmit and receive ultrasonic waves. Various types of ultrasonic transducers, such as a magnetostrictive ultrasonic transducer using a magnetostrictive effect of a magnetic material widely used in ultrasound probes, a piezoelectric ultrasonic transducer using a piezoelectric effect of a piezoelectric material, and a piezoelectric micromachined ultrasonic transducer (pMUT) may be used as the transducer element 312. Furthermore, a capacitive micromachined ultrasonic transducer (cMUT), which transmits and receives ultrasonic waves by using vibration of hundreds or thousands of micromachined thin films, may also be used. According to the illustrated exemplary embodiment, a cMUT will be described as an example of the transducer element 312.

The cMUT array 300 may include a two-dimensional (2D) array as illustrated in FIGS. 3 and 4.

A tile 310 is a basic constituent unit of the cMUT array 300. The tile 310 includes elements 312 arrayed in a 2D array form. The element 312 includes a plurality of thin films 313 which are arrayed in a 2D array form and which vibrate when an electric signal is applied thereto.

For example, as illustrated in FIG. 5, the cMUT array 300 may have a 2D array form having a 4×8 size and may include 32 tiles 310. One tile 310 may have a 2D array form which has a 16×16 size and which includes 256 elements 312. One element 312 may include between 20 and 25 thin films 313 vibrating upon application of the electric signal in order to generate ultrasonic waves. In this case, the cMUT array 300 may include a total of between 163,840 and 204,800 thin films 313.

As described above, when the cMUT array 300 that is a transducer of the ultrasound probe P has a 2D array form which has a 4×8 size and which includes 32 tiles 310, two integrated circuits 200 configured for controlling electric signals respectively applied to two upper tiles 310 and two lower tiles 310 of each row of the cMUT array 300 may be bonded thereto.

For example, the cMUT array 300 may be bonded to the integrated circuits 200, such as, for example, Application Specific Integrated Circuits (ASICs), via a film or adhesive 280. The integrated circuits 200 to which the cMUT array 300 is bonded may be connected to the control board 150 via the printed circuit board 100 and the flexible printed circuit board 171. This will be described below. When the transmit signal is applied through the control board 150, the integrated circuits 200 may control generation of ultrasonic waves by controlling the transmit signal applied to the cMUT array 300 in accordance with a logic. The transmit signal applied from the control board 150 may be a transmit pulse output from the ultrasonic wave generation controller 430 of the main body M. According to another exemplary embodiment, the control board 150 may directly generate a transmit pulse and output the transmit pulse to the integrated circuits 200 via the printed circuit board 100 and the flexible printed circuit board 171.

The film 280-1 refers to a very thin layer of a solid attached to the surface of an object, and the adhesive 280-2 refers to a material used to bond objects and solidified from a liquid state. Both of the film 280-1 and the adhesive 280-2 may be regarded as an adhesive member 280.

The printed circuit board 100 is electrically connected to the integrated circuits 200 via the film or adhesive 280, thereby transmitting the transmit signal output from the control board 150 to the integrated circuits 200. In addition, as illustrated in FIGS. 3, 4, 6, 7, and 8, the printed circuit board 100 may have a cavity in which the integrated circuits 200 are disposed, and a surface of a non-cavity region of the printed circuit board 100 bonded to the film or adhesive 280 may have a height identical to those of the integrated circuits 200 bonded to the film or adhesive 280. In particular, the printed circuit board 100 may have a height-leveled surface bonded to the film or adhesive 280.

Meanwhile, in addition to the bonding to the film or adhesive 280 by forming the cavity in the printed circuit board 100, the printed circuit board 100 may also be bonded to the film or adhesive 280 by disposing a pad (not shown) having the same height as those of the integrated circuits 200 disposed on the front surface of the printed circuit board 100, without being limited thereto.

In addition, the printed circuit board 100 may include a plurality of electrodes P at both ends thereof. The plurality of electrodes P transmit the transmit signal to electrodes P of the integrated circuits 200 via the film or adhesive 280 bonded to the printed circuit board 100 and the integrated circuits 200.

The integrated circuits 200 may control a generation of ultrasonic waves by controlling the transmit signal applied to the cMUT array 300 in accordance with a logic. The integrated circuits 200 may include electrodes P connected to the printed circuit board 100 at both ends. In particular, the electrodes E of the integrated circuits 200 receive the transmit signal from the electrodes E of the printed circuit board 100 via the film or adhesive 280 bonded to the printed circuit board 100 and the integrated circuits 200.

The transducer module T according to the illustrated exemplary embodiment may include the pad bridge 290. The pad bridge 290 connects the printed circuit board 100 with the integrated circuits 200 via the film or adhesive 280, as illustrated in FIGS. 3, 6, and 7. In particular, the pad bridge 290 is bonded to the front surfaces of the printed circuit board 100 and the integrated circuits 200 via the film or adhesive 280, and may include wiring blocks for electrical connection between the integrated circuits 200 and the printed circuit board 100.

In addition, the pad bridge 290 may enable transmission of the transmit signal from an electrode P of the printed circuit board 100 not only to electrodes P of one integrated circuit 200 adjacent thereto in the X-axis, but also to electrodes P of the other integrated circuit 200. In the same manner, any one of the electrodes E of the integrated circuits 200 may be connected to any one of the electrodes E of the printed circuit board 100 via the pad bridge 290.

Since the pad bridge 290 is connected to the plurality of electrodes P of the printed circuit board 100 and the integrated circuits 200 via the film or adhesive 280, an unnecessary area which might otherwise be required for complex wirings respectively connecting the electrodes E of the printed circuit board 100 with the electrodes E of the integrated circuits 200 may be reduced.

The flexible printed circuit board 171 transmits the transmit signal output from the control board 150 to the printed circuit board 100. In particular, since one end of the flexible printed circuit board 171 is connected to the back surface of the printed circuit board 100, and the other end of the flexible printed circuit board 171 is connected to the control board 150, the transmit signal output from the control board 150 may be transmitted to the printed circuit board 100, and thus the transmit signal is transmitted to the integrated circuits 200. The control board 150 may be implemented using a printed circuit board on which electronic devices for generating the transmit signal and processing the ultrasonic signal are mounted.

The other end of the flexible printed circuit board 171 may be connected to the control board 150 via any of various known connectors, or may be connected to electrodes of the control board 150 via an anisotropic conductive film 280-1.

As a connector to electrically connect the flexible printed circuit board 171 with the printed circuit board 100, a separate socket 110 may be disposed on the back surface of the printed circuit board 100.

Meanwhile, in the transducer module T according to another exemplary embodiment, the flexible printed circuit board 171, instead of the pad bridge 290, may be disposed on the front surfaces of the printed circuit board 100 and the integrated circuits 200, such that the flexible printed circuit board 171 may perform functions of both of the pad bridge 290 and the flexible printed circuit board 171 as illustrated in FIGS. 4 and 8.

In particular, since the flexible printed circuit board 171 is bonded to the front surfaces of the printed circuit board 100 and the integrated circuits 200, the transmit signal may be transmitted to the printed circuit board 100 via the film or adhesive 280, and the printed circuit board 100 and the integrated circuits 200 are connected to each other via the film or adhesive 280.

In addition, as illustrated in FIGS. 4 and 8, two flexible printed circuit boards 171 may be disposed on both sides of the cMUT array 300. However, exemplary embodiments are not limited thereto, one flexible printed circuit board 171 having an empty region may also be used. In particular, the empty region may be the bonding surface of the film or adhesive 280 between the cMUT array 300 and the integrated circuits 200.

As illustrated in FIGS. 3 and 4, the control board 150 may be disposed at the back side of the printed circuit board 100 to be perpendicular to the printed circuit board 100 and the integrated circuits 200, without being limited thereto.

Meanwhile, referring to FIGS. 6, 7, and 8, the transducer module T may further include a leveling unit (also referred to herein as a "leveler") 500, and the leveling unit 500 is configured to level the height of the film or adhesive 280 with respect to the surface of the cMUT array 300. In this aspect, the film or adhesive 280 functions as a cushion for a height difference of the surface of the cMUT array 300.

The film 280-1 may include any of an anisotropic conductive film (ACF), an isotropic conductive film (ICF), or a non-conductive film (NCF), and the adhesive 280-2 may include any of an anisotropic conductive adhesive (ACA), an isotropic conductive adhesive (ICA), or a non-conductive adhesive (ICA), without being limited thereto.

Hereinafter, the anisotropic conductive film 280-1, which bonds the back surface of the cMUT array 300 to the front surfaces of the printed circuit board 100 and the integrated circuits 200, will be described.

Figure 9:
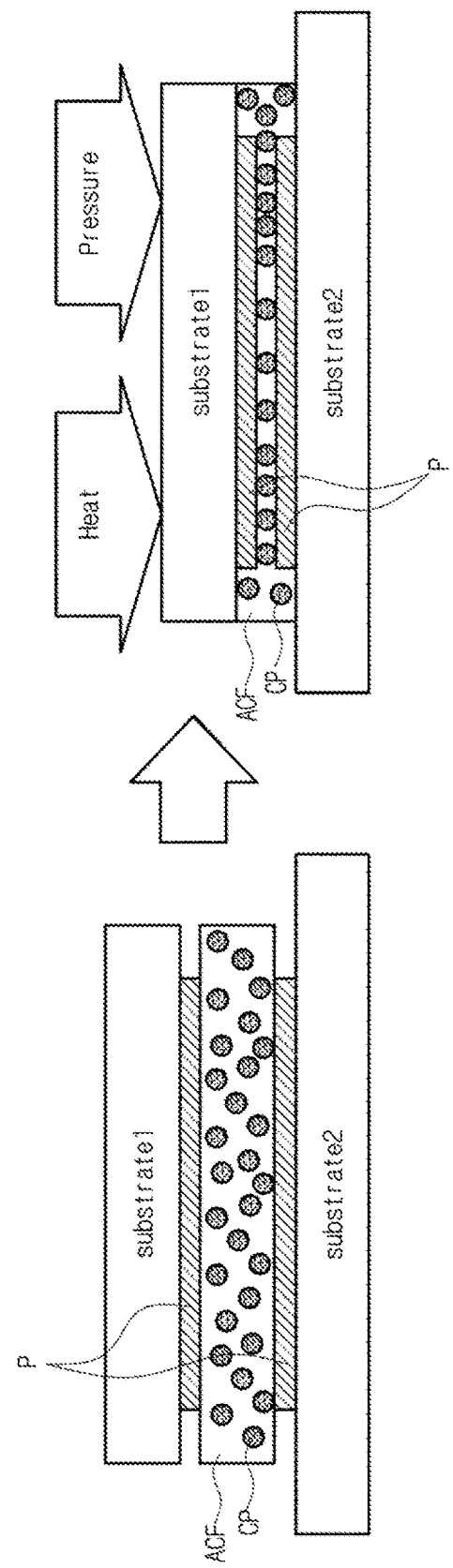
FIG. 9 is a diagram illustrating a concept of bonding by using an anisotropic conductive film.
Figure 10:
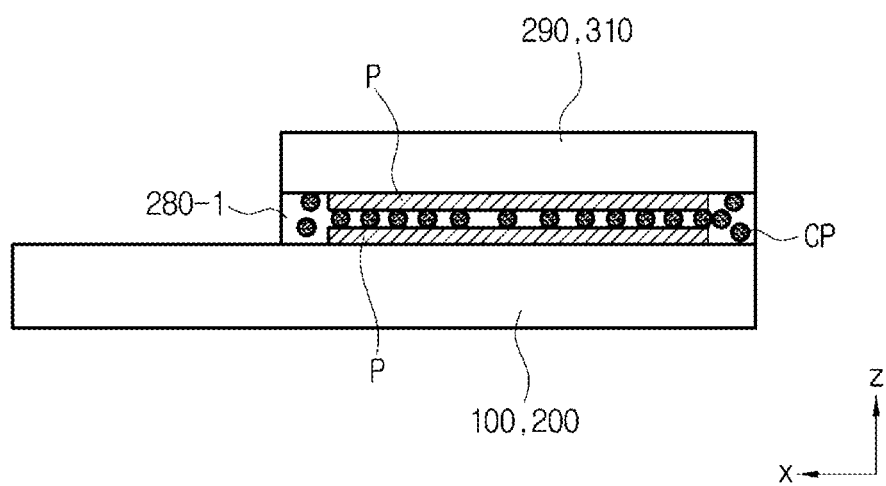
FIG. 10 is a diagram illustrating a concept of bonding of a cMUT array to an integrated circuit or bonding of a pad bridge to a printed circuit board or the integrated circuit by using an anisotropic conductive film.

FIG. 9 is a diagram illustrating a concept of bonding by using the anisotropic conductive film 280-1. FIG. 10 is a diagram illustrating a concept of bonding of the cMUT array 300 to the integrated circuits 200 or bonding of the pad bridge 290 to the printed circuit board 100 or the integrated circuits 200 by using the anisotropic conductive film 280-1.

In the anisotropic conductive film 280-1, conductive particles CP are dispersed in a film-shaped thermosetting epoxy resin or acrylic resin. Various electronic parts are mechanically or electrically bonded together by the anisotropic conductive film 280-1 through a process of applying heat and pressure.

As illustrated in FIG. 9, the anisotropic conductive film ACF 280-1 is disposed between electrodes P of objects to be bonded to each other, e.g., "substrate 1" and "substrate 2".

When heat and pressure are applied to the substrate 1, the substrate 1 and the substrate 2 are not only mechanically bonded to each other by the anisotropic conductive film ACF 280-1, but are also electrically connected to each other by the conductive particles CP dispersed in the anisotropic conductive film ACF 280-1.

Hereinafter, the anisotropic conductive film 280-1 will be described with reference to the structure including the pad bridge 290 illustrated in FIGS. 3 and 6. According to another exemplary embodiment, in the transducer module T including the flexible printed circuit board 171 illustrated in FIGS. 4 and 8, the pad bridge 290 may be implemented by using the flexible printed circuit board 171.

As illustrated in FIG. 10, when the anisotropic conductive film 280-1 is disposed between the electrodes E of the printed circuit board 100 and the electrodes E of the pad bridge 290, and heat and pressure are applied to the printed circuit board 100 or the pad bridge 290, the anisotropic conductive film 280-1 has fluidity. In addition, the conductive particles CP disposed between the electrodes E of the printed circuit board 100 and the electrodes E of the pad bridge 290 are physically connected to the electrodes E of the printed circuit board 100 and the electrodes E of the pad bridge 290, so that the electrodes E of the printed circuit board 100 and the electrodes E of the pad bridge 290 are electrically connected to each other.

When the anisotropic conductive film 280-1 is hardened, the pad bridge 290 is mechanically attached to the printed circuit board 100. The conductive particles CP of the anisotropic conductive film 280-1 electrically connects the electrodes E of the printed circuit board 100 with the electrodes E of the pad bridge 290. A signal output from the printed circuit board 100 is transmitted to the pad bridge 290 by the conductive particles CP.

In addition, when the anisotropic conductive film 280-1 is disposed between the electrodes E of the pad bridge 290 and the electrodes E of the integrated circuits 200, and heat and pressure are applied to the integrated circuits 200 or the pad bridge 290, the anisotropic conductive film 280-1 has fluidity. In addition, the conductive particles CP disposed between the electrodes E of the pad bridge 290 and the electrodes E of the integrated circuits 200 are physically connected to the electrodes E of the pad bridge 290 and the electrodes E of the integrated circuits 200, so that the electrodes E of the pad bridge 290 and the electrodes E of the integrated circuits 200 are electrically connected to each other.

When the anisotropic conductive film 280-1 is hardened, the integrated circuits 200 are mechanically attached to the pad bridge 290. In addition, the conductive particles CP of the anisotropic conductive film 280-1 electrically connect the electrodes E of the pad bridge 290 with the electrodes E of the integrated circuits 200. A signal output from the pad bridge 290 is transmitted to the integrated circuits 200 by the conductive particles CP.

In addition, when the anisotropic conductive film 280-1 is disposed between the electrodes E of the integrated circuits 200 and the electrodes of the cMUT array 300, and heat and pressure are applied to the integrated circuits 200 or the cMUT array 300, the anisotropic conductive film 280-1 has fluidity. In addition, the conductive particles CP disposed between the electrodes E of the integrated circuits 200 and the electrodes of the cMUT array 300 are physically connected to the electrodes E of the integrated circuits 200 and the electrodes E of the cMUT array 300, so that the electrodes E of the integrated circuits 200 and the electrodes E of the cMUT array 300 are electrically connected to each other.

When the anisotropic conductive film 280-1 is hardened, the cMUT array 300 is mechanically attached to the integrated circuits 200. In addition, the conductive particles CP of the anisotropic conductive film 280-1 electrically connect the electrodes E of the integrated circuits 200 with the electrodes E of the cMUT array 300. A signal output from the integrated circuits 200 is transmitted to the cMUT array 300 by the conductive particles CP.

Meanwhile, when a bonding process of the anisotropic conductive film 280-1 is performed in a vacuum environment, air-voids may be minimized in a bonding interface, thereby improving mechanical reliability. By using this bonding process of the anisotropic conductive film 280-1, an underfill process, which may be performed in a conventional flip-chip process by soldering, may be omitted.

Figure 11:
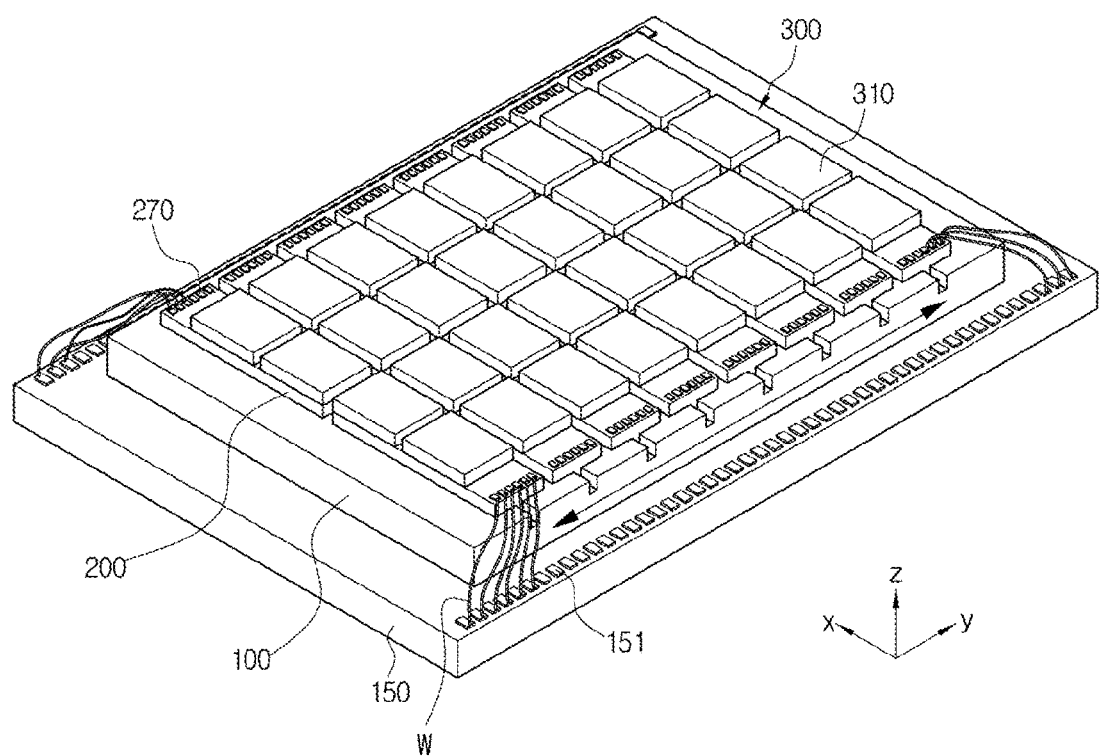
FIG. 11 is a perspective view illustrating a transducer module having a stack structure in which a control board is connected to an integrated circuit by wires.

FIG. 11 is a perspective view illustrating a transducer module having a stack structure in which a control board and integrated circuits are connected by wires.

As illustrated in FIG. 11, in general, the stack structure is formed by installing the control board 150 on the back surface of the integrated circuits 200 to be parallel to the integrated circuits 200. In addition, the integrated circuits 200 are connected to the control board 150 via wires W. In this regard, the control board 150 has an area larger than a total area of the integrated circuits 200 as illustrated in FIG. 11, such that the electrodes E of the integrated circuits 200 are connected to the control board 150 by wiring.

When a transducer module T is manufactured as illustrated in FIG. 11, a length of the integrated circuits 200 in the X-axial direction is about 2.6 cm, and a length of the control board 150 in the X-axial direction is about 5 cm, which is about twice the length of the integrated circuits 200. In this case, a length of a footprint of the ultrasound probe P in the X-axial direction is increased to about 5 cm or greater from 3 cm or less, thereby causing a reduction in transmission and reception efficiency.

In addition, when the integrated circuits 200 are connected to the control board 150 by wiring, the area of the control board 150 should be greater than a total area of the integrated circuits 200 in order to prevent interference among the wirings W and reduce difficulty of the process, so that transmission and reception efficiency may further be reduced.

According to one or more exemplary embodiments, the integrated circuits 200 are connected to the control board 150 not by wirings W, but instead, the cMUT array 300, the integrated circuits 200, the printed circuit board 100, and the pad bridge 290 are integrally connected by the film or adhesive 280, so that difficulty of the process caused by wiring may be reduced. In addition, when the cMUT array 300, the integrated circuits 200, the pad bridge 290, and the printed circuit board 100 are integrally connected using the film or adhesive 280, an area of a region of the ultrasound probe P which contacts the human body (i.e., a footprint) may be prevented from increasing to be greater than that of the integrated circuits 200.

FIG. 12 is a flowchart illustrating a method of manufacturing an ultrasound probe P, according to an exemplary embodiment.

Referring to FIG. 12, in operation 1110, the film or adhesive 280 is disposed on the front surfaces of the integrated circuits 200 and the printed circuit board 100, and the cMUT array 300 and the pad bridge 290 connecting the integrated circuits 200 with the printed circuit board 100 are disposed on the front surface of the film or adhesive 280 in operation 1120. At least one of heat and pressure is applied thereto in order to bond the integrated circuits 200, the printed circuit board 100, the pad bridge 290, and the cMUT array 300 together in operation 1130. Meanwhile, when the flexible printed circuit board 171 is disposed on the front surface of the film or adhesive 280 instead of the pad bridge 290, the film or adhesive 280 is disposed on the front surfaces of the integrated circuits 200 and the printed circuit board 100 in operation 1110, and the cMUT array 300 generating ultrasonic waves and the flexible printed circuit board 171 are disposed on the front surface of the film or adhesive 280 in operation 1120. At least one of heat and pressure is applied to bond the integrated circuits 200, the printed circuit board 100, the flexible printed circuit board 171, and the cMUT array 300 together in operation 1130.

Hereinafter, a description will be given of the pad bridge 290 disposed on the front surfaces of the printed circuit board 100 and the integrated circuits 200.

The cMUT array 300 may be bonded to the integrated circuits 200, such as Application Specific Integrated Circuits (ASICs), by using the film or adhesive 280. As described above, when the cMUT array 300, which is a transducer of the ultrasound probe P, has a 2D array form which has a 4×8 size and which includes 32 tiles 310, two integrated circuits 200 may be bonded thereto in order to control electrical signals respectively applied to two upper tiles 310 and two lower tiles 310 in each row of the cMUT array 300.

The printed circuit board 100 may be electrically connected to the integrated circuits 200 via the film or adhesive 280, thereby transmitting a transmit signal output from the control board 150 to the integrated circuits 200. In addition, as illustrated in FIGS. 3, 4, 6. 7, and 8, the printed circuit board 100 may have a cavity in which the integrated circuits 200 are disposed, and a surface of a non-cavity region of the printed circuit board 100 bonded to the film or adhesive 280 may have a height which is identical to those of the integrated circuits 200 bonded to the film or adhesive 280. In addition to the bonding to the film or adhesive 280 by forming the cavity in the printed circuit board 100, the printed circuit board 100 may also be bonded to the film or adhesive 280 by disposing a pad (not shown) having the same height as those of the integrated circuits 200 disposed on the front surface of the printed circuit board 100, without being limited thereto.

The integrated circuits 200 may control generation of ultrasonic waves by controlling the transmit signal applied to the cMUT array 300 in accordance with a logic. The electrodes E of the integrated circuits 200 receive the transmit signal from the electrodes E of the printed circuit board 100 via the film or adhesive 280 bonded to the printed circuit board 100 and the integrated circuits 200.

The pad bridge 290 is bonded to the front surfaces of the printed circuit board 100 and the integrated circuits 200 by using the film or adhesive 280, and may include wiring blocks for electrical connection between the integrated circuits 200 and the printed circuit board 100.

Next, a socket 110 is disposed on the back surface of the printed circuit board 100 in operation 1140, one end of the flexible printed circuit board 171 is connected to the socket 110 of the printed circuit board 100 in operation 1150, and the other end of the flexible printed circuit board 171 is connected to the control board 150. Thus, the transmit signal output from the control board 150 may be transmitted to the printed circuit board 100 in operation 1160.

However, when the flexible printed circuit board 171 is disposed on the front surfaces of the printed circuit board 100 and the integrated circuits 200, one end of the flexible printed circuit board 171 may be connected to the printed circuit board 100 and the integrated circuits 200 via the film or adhesive 280, and the other end of the flexible printed circuit board 171 may be connected to the control board 150. Thus, the transmit signal output from the control board 150 may be transmitted to the printed circuit board 100.

The control board 150 may be implemented using the flexible printed circuit board 171 on which electronic devices configured to generate the transmit signal and process the ultrasonic signal are mounted. In this case, the flexible printed circuit board 171 may be mounted after mounting the control board 150. Alternatively, the control board 150 may be mounted after the flexible printed circuit board 171 is bonded to the integrated circuits 200. In this aspect, the manufacturing order is not limited to the aforementioned descriptions and may vary.

The film 280-1 may include any of an anisotropic conductive film (ACF), an isotropic conductive film (ICF), or a non-conductive film (NCF), and the adhesive 280-2 may include any of an anisotropic conductive adhesive (ACA), an isotropic conductive adhesive (ICA), or a non-conductive adhesive (ICA), without being limited thereto.

In the anisotropic conductive film 280-1, conductive particles CP are dispersed in a film-shaped thermosetting epoxy resin or acrylic resin. Various electronic parts are mechanically or electrically bonded together by the anisotropic conductive film 280-1 through a process of applying heat and pressure.

As illustrated in FIG. 10, when the anisotropic conductive film 280-1 is disposed between the electrodes E of the printed circuit board 100 and the electrodes E of the pad bridge 290, and heat and pressure are applied to the printed circuit board 100 or the pad bridge 290, the anisotropic conductive film 280-1 has fluidity. In addition, the conductive particles CP disposed between the electrodes E of the printed circuit board 100 and the electrodes E of the pad bridge 290 are physically connected to the electrodes E of the printed circuit board 100 and the electrodes E of the pad bridge 290, so that the electrodes E of the printed circuit board 100 and the electrodes E of the pad bridge 290 are electrically connected to each other.

When the anisotropic conductive film 280-1 is hardened, the pad bridge 290 is mechanically attached to the printed circuit board 100. The conductive particles CP of the anisotropic conductive film 280-1 electrically connects the electrodes E of the printed circuit board 100 with the electrodes E of the pad bridge 290. A signal output from the printed circuit board 100 is transmitted to the pad bridge 290 by the conductive particles CP.

In addition, when the anisotropic conductive film 280-1 is disposed between the electrodes E of the pad bridge 290 and the electrodes E of the integrated circuits 200, and heat and pressure are applied to the integrated circuits 200 or the pad bridge 290, the anisotropic conductive film 280-1 has fluidity. In addition, the conductive particles CP disposed between the electrodes E of the pad bridge 290 and the electrodes E of the integrated circuits 200 are physically connected to the electrodes E of the pad bridge 290 and the electrodes E of the integrated circuits 200, so that the electrodes E of the pad bridge 290 and the electrodes E of the integrated circuits 200 are electrically connected to each other.

When the anisotropic conductive film 280-1 is hardened, the integrated circuits 200 are mechanically attached to the pad bridge 290. In addition, the conductive particles CP of the anisotropic conductive film 280-1 electrically connect the electrodes E of the pad bridge 290 with the electrodes E of the integrated circuits 200. A signal output from the pad bridge 290 is transmitted to the integrated circuits 200 by the conductive particles CP.

In addition, when the anisotropic conductive film 280-1 is disposed between the electrodes E of the integrated circuits 200 and the electrodes of the cMUT array 300, and heat and pressure are applied to the integrated circuits 200 or the cMUT array 300, the anisotropic conductive film 280-1 has fluidity. In addition, the conductive particles CP disposed between the electrodes E of the integrated circuits 200 and the electrodes of the cMUT array 300 are physically connected to the electrodes E of the integrated circuits 200 and the electrodes E of the cMUT array 300, so that the electrodes E of the integrated circuits 200 and the electrodes E of the cMUT array 300 are electrically connected to each other.

When the anisotropic conductive film 280-1 is hardened, the cMUT array 300 is mechanically attached to the integrated circuits 200. In addition, the conductive particles CP of the anisotropic conductive film 280-1 electrically connect the electrodes E of the integrated circuits 200 with the electrodes E of the cMUT array 300. A signal output from the integrated circuits 200 is transmitted to the cMUT array 300 by the conductive particles CP.

Meanwhile, when a bonding process of the anisotropic conductive film 280-1 is performed in a vacuum environment, air-voids may be minimized in a bonding interface, thereby improving mechanical reliability. By using this bonding process of the anisotropic conductive film 280-1, an underfill process, which is typically performed in a conventional flip-chip process by soldering, may be omitted.

As such, when the cMUT array 300, the integrated circuits 200, the printed circuit board 100, and the pad bridge 290 are integrally bonded by using the film or adhesive 280, difficulty of the process caused by wiring may be reduced. In addition, when the cMUT array 300, the integrated circuits 200, the pad bridge 290, and the printed circuit board 100 are integrally connected by using the film or adhesive 280, an area of a region of the ultrasound probe P which contacts the human body (footprint) may be prevented from increasing to be greater than that of the integrated circuits 200

As is apparent from the above description, according to exemplary embodiments, an area of a region of the ultrasound probe contacting the human body may be reduced without reducing the size of the cMUT array.

Furthermore, the integrated circuit and the printed circuit board are integrally connected not by wiring but by using the adhesive member, and thus the difficulty of the process may be reduced.

Although a few exemplary embodiments have been shown and described, it will be appreciated by those of skill in the art that changes may be made in these exemplary embodiments without departing from the principles and spirit of the present disclosure, the scope of which is defined in the claims and their equivalents.

What is claimed is:

1. An ultrasound probe comprising:
   a transducer array configured to generate ultrasonic waves;
   an integrated circuit disposed on a back surface of the transducer array via an adhesive member;
   a printed circuit board comprising a cavity that receives the integrated circuit and protruding portions on opposite sides of the cavity that extend toward the transducer array, wherein the printed circuit board is disposed on a back surface of the integrated circuit, connected to the integrated circuit, and configured to output a signal to the integrated circuit; and
   a pad bridge comprising wiring blocks disposed on one of the protruding portions of the printed circuit board and the integrated circuit via the adhesive member, wherein the pad bridge is configured to electrically connect the printed circuit board with the integrated circuit.

2. The ultrasound probe according to claim 1, wherein the adhesive member comprises at least one from among an anisotropic conductive film, an isotropic conductive film, and a non-conductive film.

3. The ultrasound probe according to claim 1, wherein the adhesive member comprises at least one from among an anisotropic conductive adhesive, an isotropic conductive adhesive, and a non-conductive adhesive.

4. The ultrasound probe according to claim 1, wherein the transducer array, the pad bridge, the integrated circuit, and the printed circuit board are bonded together by the adhesive member by using an application of heat and pressure.

5. The ultrasound probe according to claim 1, wherein the integrated circuit comprises a first plurality of electrodes and the printed circuit board comprises a second plurality of electrodes, and
   the pad bridge is further configured to electrically connect the first plurality of electrodes with the second plurality of electrodes via the adhesive member.

6. The ultrasound probe according to claim 1, further comprising:
   a flexible printed circuit board which includes a first end connected to the back surface of the printed circuit board and which is configured to output a signal to the printed circuit board; and
   a control board connected to a second end of the flexible printed circuit board and configured to output a signal to the printed circuit board via the flexible printed circuit board.

7. An ultrasound probe comprising:
   a transducer array configured to generate ultrasonic waves;
   an integrated circuit disposed on a back surface of the transducer array via an adhesive member;
   a printed circuit board comprising a cavity that receives the integrated circuit and protruding portions on opposite sides of the cavity that extend toward the transducer array, wherein the printed circuit board is disposed on a back surface of the integrated circuit, connected to the integrated circuit, and configured to output a signal to the integrated circuit; and
   a flexible printed circuit board which comprises a first end connected to at least one of the protruding portions of the printed circuit board and the integrated circuit via the adhesive member, the flexible printed circuit board also comprising a second end connected to a control board and configured to facilitate a propagation of a signal from the control board to the integrated circuit therethrough.

8. The ultrasound probe according to claim 7, wherein the adhesive member comprises at least one from among an anisotropic conductive film, an isotropic conductive film, and a non-conductive film.

9. The ultrasound probe according to claim 7, wherein the adhesive member comprises at least one from among an anisotropic conductive adhesive, an isotropic conductive adhesive, and a non-conductive adhesive.

10. The ultrasound probe according to claim 7, wherein the transducer array, the flexible printed circuit board, the integrated circuit, and the printed circuit board are bonded together by the adhesive member by using an application of heat and pressure.

11. The ultrasound probe according to claim 7, wherein the flexible printed circuit board includes an empty region, and the empty region is a region in which the transducer array is bonded to the integrated circuit.

12. The ultrasound probe according to claim 7, wherein the second end of the flexible printed circuit board is disposed at a non-zero angle with respect to the first end of the flexible printed circuit board.

* * * * *